(12) United States Patent  (10) Patent No.: US 9,561,998 B2
Yoshimoto et al.  (45) Date of Patent: Feb. 7, 2017

(54) METHOD FOR PRODUCING NITRO COMPOUND

(71) Applicant: SUMITOMO CHEMICAL COMPANY, LIMITED, Tokyo (JP)

(72) Inventors: Yuya Yoshimoto, Takarazuka (JP); Tatsuya Toriumi, Takarazuka (JP); Yuta Nagashima, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/107,872

(22) PCT Filed: Dec. 15, 2014

(86) PCT No.: PCT/JP2014/083638
§ 371 (c)(1),
(2) Date: Jun. 23, 2016

(87) PCT Pub. No.: WO2015/098717
PCT Pub. Date: Jul. 2, 2015

(65) Prior Publication Data
US 2016/0318846 A1 Nov. 3, 2016

(30) Foreign Application Priority Data

Dec. 26, 2013 (JP) ................. 2013-268642
Feb. 28, 2014 (JP) ................. 2014-038520

(51) Int. Cl.
*C07C 205/00* (2006.01)
*C07C 201/12* (2006.01)
(Continued)

(52) U.S. Cl.
CPC .......... *C07C 201/12* (2013.01); *C07C 205/34* (2013.01); *C07C 213/02* (2013.01)

(58) Field of Classification Search
CPC ..... C07C 201/12; C07C 205/34; C07C 213/02
(Continued)

(56) References Cited

U.S. PATENT DOCUMENTS 4,973,353 A 11/1990 Shida et al.
5,001,275 A 3/1991 Shida et al.
5,821,393 A 10/1998 Millauer et al.

FOREIGN PATENT DOCUMENTS

JP 63-192739 A 8/1988
JP 5-178795 A 7/1993
(Continued)

OTHER PUBLICATIONS

International Search Report for PCT/JP2014/083638 mailed on Feb. 24, 2015.
(Continued)

*Primary Examiner* — Jafar Parsa
(74) *Attorney, Agent, or Firm* — Birch, Stewart, Kolasch & Birch, LLP

(57) ABSTRACT

A nitro compound represented by formula (1) which is a raw material for producing a compound represented by formula (7) can be produced by reacting at least one type selected from the group consisting of a compound represented by formula (2), a compound represented by formula (3), and a compound represented by formula (3') with a compound represented by formula (4). [In the formula, $R^1$, $R^2$, $R^3$, and $R^4$ are each independently a hydrogen atom, etc., $X^1$ and $X^2$ are each independently a chlorine atom, etc., $R^6$, $R^7$, $R^8$, and $R^9$ are a hydrogen atom, etc., provided that $X^1$, $X^2$, $R^6$, $R^7$, $R^8$, and $R^9$ are not all the same, $X^3$, $X^4$, and $X^5$ are a halogen atom, $R^{10}$ is a nitro group, etc., $R^5$ is an alkyl group having 1 to 12 carbon atoms, etc., and M is an alkali metal atom.]

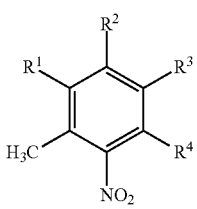

(2)

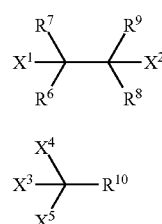

(3)
  (3')

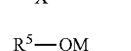

(4)

$R^5$—OM

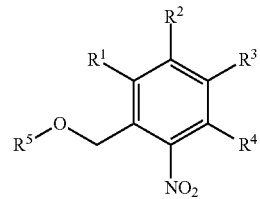 (1)

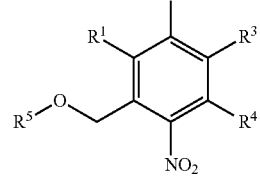

(7)

14 Claims, No Drawings

(51) Int. Cl.
*C07C 205/34* (2006.01)
*C07C 213/02* (2006.01)

(58) Field of Classification Search
USPC .................................................. 568/939, 940
See application file for complete search history.

(56) References Cited

FOREIGN PATENT DOCUMENTS

| | | |
|---|---|---|
| JP | 9-176060 A | 7/1997 |
| JP | 11-130708 A | 5/1999 |
| JP | 2006-10876 A | 1/2006 |
| JP | 2008-247824 A | 10/2008 |
| WO | WO 2012/058134 A1 | 5/2012 |
| WO | WO 2013/162072 A1 | 10/2013 |

OTHER PUBLICATIONS

Translation of the Written Opinion of the International Searching Authority dated Feb. 24, 2015, for International Application No. PCT/JP2014/083638.

METHOD FOR PRODUCING NITRO COMPOUND

TECHNICAL FIELD

The present invention relates to a method for producing a nitro compound.

BACKGROUND ART

WO 2013/162072 describes a tetrazolinone compound having an activity for controlling pests, and a compound represented by formula (7):

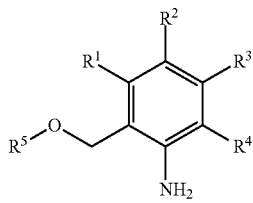

(7)

wherein $R^1$, $R^2$, $R^3$, and $R^4$ each independently represent a hydrogen atom, an alkyl group having 1 to 6 carbon atoms optionally having a halogen atom or atoms, a cycloalkyl group having 3 to 6 carbon atoms, a halogen atom, an alkoxy group having 1 to 6 carbon atoms, an alkylthio group having 1 to 6 carbon atoms, an alkylamino group having 1 to 6 carbon atoms or an aryl group having 6 to 12 carbon atoms, and $R^5$ represents an alkyl group having 1 to 12 carbon atoms, a cycloalkyl group having 3 to 6 carbon atoms or an alkenyl group having 2 to 6 carbon atoms, can be used as a production intermediate thereof.

Further, according to WO 2013/162072, 3-methyl-2-methoxymethyl-1-aminobenzene that is a typical example of the compound represented by formula (7) is produced by mixing 3-methyl-2-hydroxymethyl-1-aminobenzene, concentrated sulfuric acid, and methanol.

DISCLOSURE OF THE INVENTION

The present invention provides a method for producing a nitro compound represented by formula (1) set forth below that is a raw material for producing the compound represented by formula (7).

The present invention is as described below.

[1] A method for producing a nitro compound represented by formula (1):

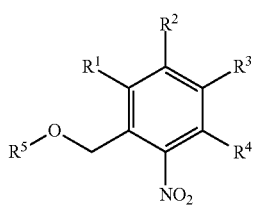

(1)

wherein $R^1$, $R^2$, $R^3$ and $R^4$ each independently represent a hydrogen atom, an alkyl group having 1 to 6 carbon atoms optionally having a halogen atom or atoms, a cycloalkyl group having 3 to 6 carbon atoms, a halogen atom, an alkoxy group having 1 to 6 carbon atoms, an alkylthio group having 1 to 6 carbon atoms, an alkylamino group having 1 to 6 carbon atoms or an aryl group having 6 to 12 carbon atoms, and $R^5$ represents an alkyl group having 1 to 12 carbon atoms, a cycloalkyl group having 3 to 6 carbon atoms or an alkenyl group having 2 to 6 carbon atoms, comprising a step of reacting a compound represented by formula (2):

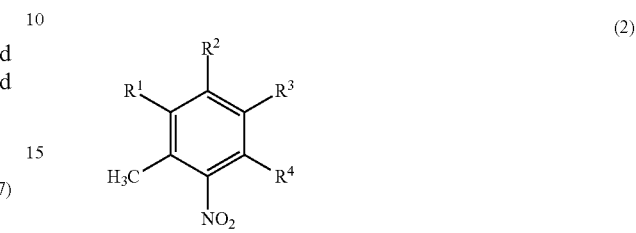

(2)

wherein $R^1$, $R^2$, $R^3$ and $R^4$ have the same meanings as above, at least one selected from the group consisting of a compound represented by formula (3):

(3)

wherein $X^1$ and $X^2$ each independently represent a chlorine atom, a bromine atom or an iodine atom, $R^6$, $R^7$, $R^8$ and $R^9$ each independently represent a halogen atom, an alkyl group having 1 to 6 carbon atoms optionally having a halogen atom or atoms, an alkenyl group having 2 to 6 carbon atoms, an alkoxy group having 1 to 6 carbon atoms, an alkoxycarbonyl group having 2 to 6 carbon atoms, a hydrogen atom or a cyano group, provided that $X^1$, $X^2$, $R^6$, $R^7$, $R^8$ and $R^9$ are not all the same, and $R^7$ and $R^9$ may be bonded each other to form a ring together with the carbon atoms to which they are bonded, and a compound represented by formula (3'):

(3')

wherein $X^3$, $X^4$ and $X^5$ represent a halogen atom, and $R^{10}$ represents a hydrogen atom, a nitro group, a halogen atom, an alkyl group having 1 to 6 carbon atoms optionally having a halogen atom or atoms, an alkoxy group having 1 to 6 carbon atoms or an aryl group having 6 to 12 carbon atoms, and a compound represented by formula (4):

$R^5$—OM (4)

wherein $R^5$ has the same meaning as above, and M represents an alkali metal atom.

[2] The method for producing a nitro compound according to [1] comprising a step of reacting the compound represented by formula (2), the compound represented by formula (3), and the compound represented by formula (4).

[3] A method for producing a nitro compound represented by formula (1):

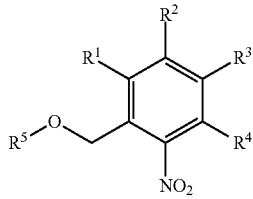
(1)

wherein $R^1$, $R^2$, $R^3$ and $R^4$ each independently represent a hydrogen atom, an alkyl group having 1 to 6 carbon atoms optionally having a halogen atom or atoms, a cycloalkyl group having 3 to 6 carbon atoms, a halogen atom, an alkoxy group having 1 to 6 carbon atoms, an alkylthio group having 1 to 6 carbon atoms, an alkylamino group having 1 to 6 carbon atoms or an aryl group having 6 to 12 carbon atoms, and $R^5$ represents an alkyl group having 1 to 12 carbon atoms, a cycloalkyl group having 3 to 6 carbon atoms or an alkenyl group having 2 to 6 carbon atoms, comprising a step of reacting a compound represented by formula (5):

wherein $R^5$ has the same meaning as above, a compound represented by formula (6):

wherein M represents an alkali metal atom, a compound represented by formula (2):

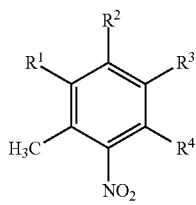
(2)

wherein $R^1$, $R^2$, $R^3$ and $R^4$ have the same meanings as above, and at least one selected from the group consisting of a compound represented by formula (3):

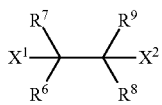
(3)

wherein $X^1$ and $X^2$ each independently represent a chlorine atom, a bromine atom or an iodine atom, $R^6$, $R^7$, $R^8$ and $R^9$ each independently represent a halogen atom, an alkyl group having 1 to 6 carbon atoms optionally having a halogen atom or atoms, an alkenyl group having 2 to 6 carbon atoms, an alkoxy group having 1 to 6 carbon atoms, an alkoxycarbonyl group having 2 to 6 carbon atoms, a hydrogen atom or a cyano group, provided that $X^1$, $X^2$, $R^6$, $R^7$, $R^8$ and $R^9$ are not all the same, and $R^7$ and $R^9$ may be bonded each other to form a ring together with the carbon atoms to which they are bonded, and a compound represented by formula (3'):

(3')

wherein $X^3$, $X^4$ and $X^5$ represent a halogen atom, and $R^{10}$ represents a hydrogen atom, a nitro group, a halogen atom, an alkyl group having 1 to 6 carbon atoms optionally having a halogen atom or atoms, an alkoxy group having 1 to 6 carbon atoms or an aryl group having 6 to 12 carbon atoms.

[4] The method for producing a nitro compound according to [3] comprising a step of reacting the compound represented by formula (5), the compound represented by formula (6), the compound represented by formula (2), and the compound represented by formula (3).

[5] The production method according to [2] or [4], wherein $X^1$ and $X^2$ are the same.

[6] The production method according to [2] or [4], wherein the compound represented by the formula (3) is 1,2-dibromo-1,1,2,2-tetrachloroethane or 1,2-dibromo-1,1,2,2-tetrafluoroethane.

[7] The method for producing a nitro compound according to [1] comprising a step of reacting the compound represented by formula (2), the compound represented by formula (3'), and the compound represented by formula (4).

[8] The method for producing a nitro compound according to [3] comprising a step of reacting the compound represented by formula (5), the compound represented by formula (6), the compound represented by formula (2), and the compound represented by formula (3').

[9] The method for producing a nitro compound according to [7] or [8], wherein $R^{10}$ is a halogen atom.

[10] The method for producing a nitro compound according to [7] or [8], wherein the compound represented by formula (3') is tetrabromomethane or bromotrichloromethane.

[11] A method for producing a compound represented by formula (7):

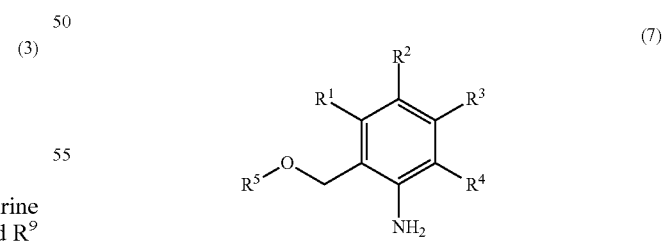
(7)

wherein $R^1$, $R^2$, $R^3$, $R^4$ and $R^5$ have the same meanings as above, comprising obtaining a nitro compound represented by formula (1) by the production method as defined in any of [1] to [10], and reducing the nitro compound represented by formula (1).

[12] A nitro compound represented by formula (8):

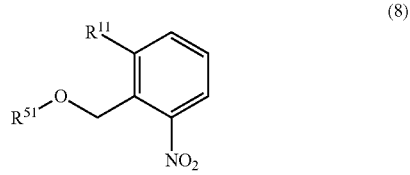

wherein $R^{11}$ represents an alkyl group having 1 to 3 carbon atoms or a cycloalkyl group having 3 to 4 carbon atoms, and $R^{51}$ represents an alkyl group having 1 to 12 carbon atoms, a cycloalkyl group having 3 to 6 carbon atoms or an alkenyl group having 2 to 6 carbon atoms.

[13] The nitro compound according to [12], wherein $R^{11}$ is a methyl group, and $R^{51}$ is an alkyl group having 1 to 6 carbon atoms.

[14] The nitro compound according to [12], wherein $R^{11}$ is a methyl group, and $R^{51}$ is a methyl group or an ethyl group.

MODE FOR CARRYING OUT THE INVENTION

First, a method for producing a nitro compound represented by a formula (1) (hereinafter, may be referred to as nitro compound (1)) will be described.

In the formula of a compound represented by formula (2)

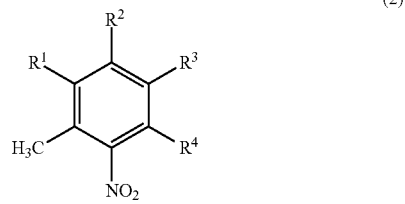

(hereinafter, may be referred to as compound (2)), $R^1$, $R^2$, $R^3$ and $R^4$ each independently represent a hydrogen atom, an alkyl group having 1 to 6 carbon atoms optionally having a halogen atom or atoms, a cycloalkyl group having 3 to 6 carbon atoms, a halogen atom, an alkoxy group having 1 to 6 carbon atoms, an alkylthio group having 1 to 6 carbon atoms, an alkylamino group having 1 to 6 carbon atoms or an aryl group having 6 to 12 carbon atoms.

The halogen atom in $R^1$, $R^2$, $R^3$ and $R^4$ is a fluorine atom, a chloride atom, a bromine atom or an iodine atom.

Examples of the alkyl group having 1 to 6 carbon atoms in $R^1$, $R^2$, $R^3$ and $R^4$ include a methyl group, an ethyl group, a propyl group, an isopropyl group, a butyl group, a sec-butyl group, a tert-butyl group, a pentyl group and a hexyl group, and it is preferably a methyl group, an ethyl group, a propyl group and an isopropyl group.

Examples of the alkyl group having 1 to 6 carbon atoms having a halogen atom or atoms in $R^1$, $R^2$, $R^3$ and $R^4$ include a trifluoromethyl group, a difluoromethyl group, a perfluoroethyl group, a perfluoropropyl group, a perfluoroisopropyl group, a perfluorobutyl group, a perfluoro sec-butyl group, a perfluoro tert-butyl group, a perfluoropentyl group, a perfluorohexyl group, a trichloromethyl group, a tribromomethyl group and a triiodomethyl group, and it is preferably a trifluoromethyl group and a difluoromethyl group.

Examples of the cycloalkyl group having 3 to 6 carbon atoms in $R^1$, $R^2$, $R^3$ and $R^4$ include a cyclopropyl group, a cyclobutyl group, a cyclopentyl group and a cyclohexyl group, and it is preferably a cyclopropyl group and a cyclobutyl group.

Examples of the alkoxy group having 1 to 6 carbon atoms in $R^1$, $R^2$, $R^3$ and $R^4$ include a methoxy group, an ethoxy group, a propoxy group, an isopropoxy group, a butoxy group, a pentyloxy group and a hexyloxy group, and it is preferably a methoxy group, an ethoxy group, a propoxy group and an isopropoxy group.

Examples of the alkylthio group having 1 to 6 carbon atoms in $R^1$, $R^2$, $R^3$ and $R^4$ include a methylthio group, an ethylthio group, a propylthio group, a butylthio group, a pentylthio group and a hexylthio group, and it is preferably an alkylthio group having 1 to 3 carbon atoms.

Examples of the alkylamino group having 1 to 6 carbon atoms in $R^1$, $R^2$, $R^3$ and $R^4$ include a N-methylamino group, an N-ethylamino group, a N-propylamino group, an N-isopropylamino group, a N,N-dimethylamino group, a N,N-diethylamino group and a N-methyl-N-ethylamino group, and it is preferably an alkylamino group having 1 to 3 carbon atoms.

Examples of the aryl group having 6 to 12 carbon atoms in $R^1$, $R^2$, $R^3$ and $R^4$ include a phenyl group, a naphthyl group and a tolyl group, and it is preferably an aryl group having 6 to 8 carbon atoms.

$R^1$ is preferably an alkyl group having 1 to 6 carbon atoms or a cycloalkyl group having 3 to 6 carbon atoms, more preferably an alkyl group having 1 to 3 carbon atoms or a cycloalkyl group having 3 to 4 carbon atoms, and further preferably a methyl group.

$R^2$, $R^3$ and $R^4$ are preferably a hydrogen atom.

Examples of compound (2) include 2,3-dimethylnitrobenzene, 2-methylnitrobenzene, 2-methyl-3-ethylnitrobenzene, 2-methyl-3-cyclopropylnitrobenzene, 2-methyl-3-trifluoromethylnitrobenzene, 2-methyl-3-difluoromethylnitrobenzene, 2-methyl-3-chloronitrobenzene, 2-methyl-3-bromonitrobenzene, 2-methyl-3-fluoronitrobenzene, 2-methyl-3-iodonitrobenzene, 2-methyl-3-methoxynitrobenzene, 2-methyl-3-ethoxynitrobenzene, 2-methyl-3-methylthionitrobenzene and 2-methyl-3-(N,N-dimethylamino)nitrobenzene.

A commercially available compound (2) may be used, and for example, it may be produced according to the method described in Journal of the American Chemical Society, 1940, vol. 62, p. 141.

In the formula of the compound represented by formula (3):

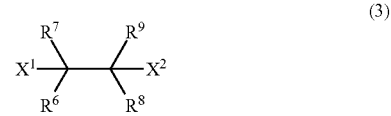

(hereinafter, may be referred to as compound (3)), $X^1$ and $X^2$ each independently represent a chlorine atom, a bromine atom or an iodine atom, $R^6$, $R^7$, $R^8$ and $R^9$ each independently represent a halogen atom, an alkyl group having 1 to 6 carbon atoms optionally having a halogen atom or atoms, an alkenyl group having 2 to 6 carbon atoms, an alkoxy group having 1 to 6 carbon atoms, an alkoxycarbonyl group having 2 to 6 carbon atoms, a hydrogen atom or a cyano group, provided that $X^1$, $X^2$, $R^6$, $R^7$, $R^8$ and $R^9$ are not all the same, and $R^7$ and $R^9$ may be bonded each other to form a ring such as a cyclopropane ring, a cyclobutane ring, a cyclopentane ring and a cyclohexane ring, together with the carbon atoms to which they are bonded. In the case of forming a ring, it is preferred to form a cyclopentane ring or a cyclohexane ring.

The halogen atom, the alkyl group having 1 to 6 carbon atoms optionally having a halogen atom or atoms and the alkoxy group having 1 to 6 carbon atoms in $R^6$, $R^7$, $R^8$ and $R^9$ include the same groups as described above.

Examples of the alkenyl group having 2 to 6 carbon atoms in $R^6$, $R^7$, $R^8$ and $R^9$ include a vinyl group, an allyl group, a 1-propenyl group and a 1-methyl-2-propenyl group, and it is preferably a vinyl group, an allyl group and a 1-propenyl group.

Examples of the alkoxycarbonyl group having 2 to 6 carbon atoms in $R^6$, $R^7$, $R^8$ and $R^9$ include a methoxycarbonyl group, an ethoxycarbonyl group, a propoxycarbonyl group, an isopropoxycarbonyl group and a butoxycarbonyl group, and it is preferably a methoxycarbonyl group, an ethoxycarbonyl group, a propoxycarbonyl group and an isopropoxycarbonyl group.

$R^6$, $R^7$, $R^8$ and $R^9$ are preferably a halogen atom, and the halogen atom is more preferably a chlorine atom.

$R^6$, $R^7$, $R^8$ and $R^9$ are preferably all the same.

$X^1$ and $X^2$ each independently represent a chlorine atom, a bromine atom or an iodine atom, and $X^1$ and $X^2$ are preferably the same.

$X^1$, and $X^2$ are preferably both a bromine atom.

$X^1$ and $X^2$ are preferably the same, and when $R^6$, $R^7$, $R^8$ and $R^9$ are a halogen atom, $R^6$, $R^7$, $R^8$ and $R^9$ are preferably a halogen atom different from $X^1$ and $X^2$.

Specific examples of compound (3) are 1,2-dibromo-1,1,2,2-tetrachloroethane and 1,2-dibromo-1,1,2,2-tetrafluoroethane, and a preferred example is 1,2-dibromo-1,1,2,2-tetrachloroethane.

A commercially available compound (3) may be used, and for example, it may be produced according to the method described in Organic Letters, 2004, vol. 6, p. 2701 using a corresponding alkene and halogen.

In the formula of the compound represented by formula (3'):

(3')

(hereinafter, may be referred to as compound (3')), $X^3$, $X^4$ and $X^5$ represent a halogen atom, and $R^{10}$ represents a hydrogen atom, a nitro group, a halogen atom, an alkyl group having 1 to 6 carbon atoms optionally having a halogen atom or atoms, an alkoxy group having 1 to 6 carbon atoms or an aryl group having 6 to 12 carbon atoms.

$X^3$, $X^4$ and $X^5$ represent a halogen atom. The halogen atom in $X^3$, $X^4$ and $X^5$ includes a fluorine atom, a chlorine atom, a bromine atom and an iodine atom. It is preferred that at least two of $X^3$, $X^4$ and $X^5$ are the same each other, and it is more preferred that $X^3$, $X^4$ and $X^5$ are all the same.

$R^{10}$ represents a hydrogen atom, a nitro group, a halogen atom, an alkyl group having 1 to 6 carbon atoms optionally having a halogen atom or atoms, an alkoxy group having 1 to 6 carbon atoms or an aryl group having 6 to 12 carbon atoms. The halogen atom in $R^{10}$ includes a fluorine atom, a chlorine atom, a bromine atom and an iodine atom. Examples of the alkyl group having 1 to 6 carbon atoms optionally having a halogen atom or atoms in $R^{10}$ include a methyl group, an ethyl group, a propyl group, an isopropyl group, a butyl group, a sec-butyl group, a tert-butyl group, a pentyl group, a hexyl group, a trifluoromethyl group, a difluoromethyl group, a perfluoroethyl group, a perfluoropropyl group, a perfluoroisopropyl group, a perfluorobutyl group, a perfluoro sec-butyl group, a perfluoro tert-butyl group, a perfluoropentyl group, a perfluorohexyl group, a trichloromethyl group, a tribromomethyl group and a triiodomethyl group, and it is preferably an alkyl group having 1 to 3 carbon atoms, a trifluoromethyl group, and a difluoromethyl group. Examples of the alkoxy group having 1 to 6 carbon atoms in $R^{10}$ include a methoxy group, an ethoxy group, a propoxy group, an isopropoxy group, a butoxy group, a pentyloxy group and a hexyloxy group, and it is preferably an alkoxy group having 1 to 3 carbon atoms. Examples of the aryl group having 6 to 12 carbon atoms in $R^{10}$ include a phenyl group, a naphthyl group and a tolyl group, and it is preferably an aryl group having 6 to 8 carbon atoms.

$R^{10}$ is preferably a nitro group or a halogen atom, more preferably a halogen atom, and particularly preferably a halogen atom different from $X^3$, $X^4$ and $X^5$.

Examples of compound (3') include tetrachloromethane, tetrabromomethane, bromotrichloromethane, tribromoiodomethane, bromotrifluoromethane, bromochlorodifluoromethane and tribromonitromethane, and is preferably tetrabromomethane, bromotrichloromethane, tribromoiodomethane, bromotrifluoromethane and bromochlorodifluoromethane, and more preferably tetrabromomethane and bromotrichloromethane.

Compound (3) and compound (3') may be both used, and compound (3) or compound (3') may be used alone.

The used amount of at least one selected from the group consisting of compound (3) and compound (3') is usually a ratio of 0.2 to 10 mol, preferably a ratio of 0.5 to 5 mol, more preferably a ratio of 1 to 5 mol, and further preferably a ratio of 1 to 4 mol, based on 1 mol of compound (2).

In the formula of the compound represented by formula (4):

$R^5$—OM (4)

(hereinafter, may be referred to as compound (4)), $R^5$ represents an alkyl group having 1 to 12 carbon atoms, a cycloalkyl group having 3 to 6 carbon atoms or an alkenyl group having 2 to 6 carbon atoms, and M represents an alkali metal atom.

Examples of the alkyl group having 1 to 12 carbon atoms in $R^5$ include a methyl group, an ethyl group, a propyl group, an isopropyl group, a butyl group, a sec-butyl group, a tert-butyl group, a pentyl group, a hexyl group, a nonyl group, a decyl group, an undecyl group and a dodecyl group, and it is preferably an alkyl group having 1 to 6 carbon atoms.

Examples of the cycloalkyl group having 3 to 6 carbon atoms in $R^5$ include a cyclopropyl group, a cyclobutyl group, a cyclopentyl group and a cyclohexyl group, and it is preferably a cycloalkyl group having 3 to 6 carbon atoms.

Examples of the alkenyl group having 2 to 6 carbon atoms in $R^5$ include a vinyl group, an allyl group, a 1-propenyl group and a 1-methyl-2-propenyl group, and it is preferably an alkenyl group having 2 to 3 carbon atoms.

$R^5$ is preferably an alkyl group having 1 to 12 carbon atoms, more preferably an alkyl group having 1 to 6 carbon atoms, and further more preferably a methyl group or an ethyl group.

Examples of compound (4) include sodium methoxide, sodium ethoxide, sodium isopropoxide, sodium propoxide, sodium tert-butoxide, potassium methoxide, potassium ethoxide, potassium isopropoxide, potassium propoxide, potassium tert-butoxide, lithium methoxide, lithium ethoxide, lithium isopropoxide, lithium propoxide and lithium tert-butoxide, and is preferably sodium methoxide and sodium ethoxide.

A commercially available compound (4) may be used, and for example, one produced by preparing according to a method of reacting an alkali metal hydroxide, an alkali metal hydride or an alkali metal with a corresponding alcohol may be used, and it may be prepared according to the method in a reaction system.

The alkali metal hydride can be a compound represented by formula (6):

$$M\text{-}OH \qquad (6)$$

wherein M represents an alkali metal atom, (hereinafter, may be referred to as compound (6)).

Examples of the alkali metal in M include a sodium atom, a potassium atom and a lithium atom, and is preferably a sodium atom and a potassium atom.

Examples of the compound (6) include sodium hydroxide, potassium hydroxide and lithium hydroxide, and it is preferably sodium hydroxide and potassium hydroxide.

Examples of the alkali metal hydride include lithium hydride, sodium hydride and potassium hydride.

Examples of the alkali metal include a lithium atom, a sodium atom and a potassium atom.

The corresponding alcohol can be a compound represented by formula (5):

$$R^5\text{---}OH \qquad (5)$$

wherein $R^5$ has the same meaning as above,
(hereinafter, may be referred to as compound (5)). Examples of compound (5) include methanol, ethanol, propanol, isopropyl alcohol, tert-butyl alcohol, cyclopropanol, cyclohexanol and 2-propen-1-ol, and it is preferably methanol and ethanol.

The used amount of compound (4) is usually 1 to 100 mol, and preferably 1 to 10 mol, based on 1 mol of compound (2).

The nitro compound (1) can be produced by reacting compound (4), compound (2), and at least one selected from the group consisting of compound (3) and compound (3'). In the reaction, these should be mixed in an arbitrary order. For example, compound (4) may be added to a mixture of at least one selected from the group consisting of compound (3) and compound (3') and compound (2), and at least one selected from the group consisting of compound (3) and compound (3') may be added to a mixture of compound (2) and compound (4). Compound (4) and at least one selected from the group consisting of compound (3) and compound (3') may be simultaneously added to compound (2) in parallel.

Compound (2) may be mixed all at once, and may be mixed one by one.

Compound (3) or compound (3') also may be mixed all at once, and may be mixed one by one.

The reaction may be carried out under a nitrogen atmosphere.

The reaction temperature is usually within the range of −20 to 150° C., and preferably within the range of 0 to 100° C. The reaction time is usually 0.1 to 72 hours, and preferably 1 to 24 hours.

The reaction of compound (4), compound (2) and compound (3) or compound (3') may be carried out in a solvent. Examples of the solvent include methanol, ethanol, propanol, isopropyl alcohol and tert-butyl alcohol.

Nitro compound (1) can be usually produced by reacting compound (5), compound (6), compound (2), and at least one selected from the group consisting of compound (3) and compound (3'). In the reaction, these should be mixed in an arbitrary order. For example, compound (6) may be added to a mixture of compound (2), compound (5), and at least one selected from the group consisting of compound (3) and compound (3'), and in this case, a part of the compound (5) may be simultaneously added with compound (6) in parallel. At least one selected from the group consisting of compound (3) and compound (3') may be added to a mixture of compound (2), compound (5), and compound (6). Compound (5), compound (6), and at least one selected from the group consisting of compound (3) and compound (3') may be simultaneously added to compound (2) in parallel.

At least one selected from the group consisting of compound (3) and compound (3') may be mixed all at once, and may be mixed one by one, and compound (6) also may be mixed all at once, and may be mixed one by one. Furthermore, compound (5) also may be mixed all at once, and may be mixed one by one.

The used amount of compound (5) is usually in a ratio of 1 to 100 mol, and preferably in a ratio of 1 to 10 mol, based on 1 mol of compound (2).

The used amount of compound (6) is usually in a ratio of 1 to 100 mol, and preferably in a ratio of 1 to 10 mol, based on 1 mol of compound (2).

The reaction may be carried out under a nitrogen atmosphere.

The reaction temperature is usually within the range of −20 to 150° C., and preferably within the range of 0 to 100° C.

The reaction time is usually 0.1 to 72 hours, and preferably 1 to 24 hours.

The reaction may be performed while removing a by-product produced in the reaction out of the reaction system.

After the completion of the reaction, nitro compound (1) can be taken out by concentrating the obtained reaction mixture. An acid or ammonium chloride may be added to the obtained reaction mixture, as necessary.

The acid includes hydrogen chloride and sulfuric acid.

The acid or ammonium chloride may be mixed with a solvent and added. The solvent includes water and the like. When a mixture of the acid or ammonium chloride and the solvent is added, the concentration of the acid in the mixture is usually 1 to 6 N, and the concentration of ammonium chloride is usually 1 to 6 M.

The obtained nitro compound (1) can be purified by a usual purification means such as washing, distillation, or column chromatography.

Examples of nitro compound (1) includes 2-methoxymethyl-3-methyl-1-nitrobenzene, 2-ethoxymethyl-3-methyl-1-nitrobenzene, 2-isopropoxymethyl-3-methyl-1-nitrobenzene, 2-propoxymethyl-3-methyl-1-nitrobenzene, 2-(tert-butoxymethyl)-3-methyl-1-nitrobenzene, 2-methoxymethyl-3-ethyl-1-nitrobenzene, 2-ethoxymethyl-3-ethyl-1-nitrobenzene, 2-isopropoxymethyl-3-ethyl-1-nitrobenzene, 2-propoxymethyl-3-ethyl-1-nitrobenzene, 2-(tert-butoxymethyl)-3-ethyl-1-nitrobenzene, 2-methoxymethyl-3-cyclopropyl-1-nitrobenzene, 2-ethoxymethyl-3-cyclopropyl-1-nitrobenzene, 2-isopropoxymethyl-3-cyclopropyl-1-nitrobenzene, 2-propoxymethyl-3-cyclopropyl-1-nitrobenzene, 2-(tert-butoxymethyl)-3-cyclopropyl-1-nitrobenzene, 2-methoxymethyl-1-nitrobenzene, 2-ethoxymethyl-1-nitrobenzene, 2-isopropoxymethyl-1-nitrobenzene, 2-propoxymethyl-1-nitrobenzene, 2-(tert-butoxymethyl)-1-nitrobenzene, 2-methoxymethyl-3-chloro-1-nitrobenzene, 2-ethoxymethyl-3-chloro-1-nitrobenzene, 2-isopropoxymethyl-3- chloro-1-nitrobenzene, 2-propoxymethyl-3-chloro-1-nitrobenzene, 2-(tert-butoxymethyl)-3-chloro-1-nitrobenzene, 2-methoxymethyl-3-bromo-1-nitrobenzene, 2-ethoxymethyl-3-bromo-1-nitrobenzene, 2-isopropoxymethyl-3-bromo-1-nitrobenzene, 2-propoxymethyl-3-bromo-1-nitrobenzene, 2-(tert-butoxymethyl)-3-bromo-1-nitrobenzene, 2-methoxymethyl-3-fluoro-1-nitrobenzene, 2-ethoxymethyl-3-fluoro-1-nitrobenzene, 2-isopropoxymethyl-3-fluoro-1-nitrobenzene, 2-propoxymethyl-3-fluoro-1-nitrobenzene, 2-(tert-butoxymethyl)-3-fluoro-1-nitrobenzene, 2-methoxymethyl-3-methoxy-1-nitrobenzene, 2-ethoxymethyl-3-methoxy-1-nitrobenzene, 2-isopropoxymethyl-3-methoxy-1-nitrobenzene, 2-propoxymethyl-3-methoxy-1-nitrobenzene and 2-(tert-butoxymethyl)-3-methoxy-1-nitrobenzene, 2-cyclopropoxymethyl-3-methyl-1-nitrobenzene, 2-cyclobutyloxymethyl-3-methyl-1-nitrobenzene, 2-cyclopentyloxymethyl-3-methyl-1-nitrobenzene, 2-cyclohexyloxymethyl-3-methyl-1-nitrobenzene, 2-vinyloxymethyl-3-methyl-1-nitrobenzene, 2-(2-propenyloxymethyl)-3-methyl-1-nitrobenzene, 2-cyclopropoxymethyl-3-ethyl-1-nitrobenzene, 2-cyclobutyloxymethyl-3-ethyl-1-nitrobenzene, 2-cyclopentyloxymethyl-3-ethyl-1-nitrobenzene, 2-cyclohexyloxymethyl-3-ethyl-1-nitrobenzene, 2-vinyloxymethyl-3-ethyl-1-nitrobenzene, 2-(2-propenyloxymethyl)-3-ethyl-1-nitrobenzene, 2-cyclopropoxymethyl-3-cyclopropyl-1-nitrobenzene, 2-cyclobutyloxymethyl-3-cyclopropyl-1-nitrobenzene, 2-cyclopentyloxymethyl-3-cyclopropyl-1-nitrobenzene, 2-cyclohexyloxymethyl-3-cyclopropyl-1-nitrobenzene, 2-vinyloxymethyl-3-cyclopropyl-1-nitrobenzene, 2-(2-propenyloxymethyl)-3-cyclopropyl-1-nitrobenzene, 2-cyclopropoxymethyl-1-nitrobenzene, 2-cyclobutyloxymethyl-1-nitrobenzene, 2-cyclopentyloxymethyl-1-nitrobenzene, 2-cyclohexyloxymethyl-1-nitrobenzene, 2-vinyloxymethyl-1-nitrobenzene and 2-(2-propenyloxymethyl)-1-nitrobenzene.

Among the nitro compounds represented by formula (1), compounds represented by formula (8) are preferable.

The alkyl group having 1 to 3 carbon atoms in $R^{11}$ includes a methyl group, an ethyl group, a propyl group and an isopropyl group, and is preferably a methyl group.

The cycloalkyl group having 3 to 4 carbon atoms in $R^{11}$ includes a cyclopropyl group and a cyclobutyl group, and is preferably a cycloalkyl group.

$R^{11}$ is preferably a methyl group.

The alkyl group having 1 to 12 carbon atoms in $R^{51}$, the cycloalkyl group having 3 to 6 carbon atoms or the alkenyl group having 2 to 6 carbon atoms includes the groups cited in $R^5$.

$R^{51}$ is preferably an alkyl group having 1 to 6 carbon atoms, and more preferably a methyl group and an ethyl group.

The compound represented by formula (8) includes 2-methoxymethyl-3-methyl-1-nitrobenzene, 2-ethoxymethyl-3-methyl-1-nitrobenzene, 2-isopropoxymethyl-3-methyl-1-nitrobenzene, 2-propoxymethyl-3-methyl-1-nitrobenzene, 2-(tert-butoxymethyl)-3-methyl-1-nitrobenzene, 2-cyclopropoxymethyl-3-methyl-1-nitrobenzene, 2-cyclobutyloxymethyl-3-methyl-1-nitrobenzene, 2-cyclopentyloxymethyl-3-methyl-1-nitrobenzene, 2-cyclohexyloxymethyl-3-methyl-1-nitrobenzene, 2-vinyloxymethyl-3-methyl-1-nitrobenzene, 2-(2-propenyloxymethyl)-3-methyl-1-nitrobenzene, 2-methoxymethyl-3-ethyl-1-nitrobenzene, 2-ethoxymethyl-3-ethyl-1-nitrobenzene, 2-isopropoxymethyl-3-ethyl-1-nitrobenzene, 2-propoxymethyl-3-ethyl-1-nitrobenzene, 2-(tert-butoxymethyl)-3-ethyl-1-nitrobenzene, 2-cyclopropoxymethyl-3-ethyl-1-nitrobenzene, 2-cyclobutyloxymethyl-3-ethyl-1-nitrobenzene, 2-cyclopentyloxymethyl-3-ethyl-1-nitrobenzene, 2-cyclohexyloxymethyl-3-ethyl-1-nitrobenzene, 2-vinyloxymethyl-3-ethyl-1-nitrobenzene, 2-(2-propenyloxymethyl)-3-ethyl-1-nitrobenzene, 2-methoxymethyl-3-cyclopropyl-1-nitrobenzene, 2-ethoxymethyl-3-cyclopropyl-1-nitrobenzene, 2-isopropoxymethyl-3-cyclopropyl-1-nitrobenzene, 2-propoxymethyl-3-cyclopropyl-1-nitrobenzene, 2-(tert-butoxymethyl)-3-cyclopropyl-1-nitrobenzene, 2-cyclopropoxymethyl-3-cyclopropyl-1-nitrobenzene, 2-cyclobutyloxymethyl-3-cyclopropyl-1-nitrobenzene, 2-cyclopentyloxymethyl-3-cyclopropyl-1-nitrobenzene, 2-cyclohexyloxymethyl-3-cyclopropyl-1-nitrobenzene, 2-vinyloxymethyl-3-cyclopropyl-1-nitrobenzene, and 2-(2-propenyloxymethyl)-3-cyclopropyl-1-nitrobenzene.

Next, the method for producing a compound represented by formula (7) will be described.

The compound represented by formula (7) can be produced by reducing the nitro compound represented by formula (1). The reduction method is preferably a method for reacting the nitro compound represented by formula (1) with hydrogen, in the presence of a transition metal catalyst.

The transition metal catalysts are nickel catalysts such as nickel sponge: noble metal catalyst such as palladium, ruthenium, rhodium, osmium, platinum, iridium, and the like.

The transition metal catalyst may be carried on a carrier. The carrier includes activated carbon, alumina, silica, zeolite, and the like, and preferred transition metal catalyst is palladium-carbon and platinum-carbon.

In the present invention, a commercially available transition metal catalyst may be used, and one prepared by any known method may be used.

The used amount of the transition metal catalyst is usually in a ratio of 0.0001 to 10 parts by weight, and preferably in a ratio of 0.001 to 1 part by weight, based on 1 part by weight of the nitro compound represented by formula (1).

As hydrogen, a hydrogen gas can be used, and for example, can be generated from a hydrogen source such as formic acid by a known method, and used. When using a hydrogen gas, its partial pressure is usually 1 MPa or less, and preferably 0.1 MPa.

The reaction of the nitro compound represented by formula (1) with hydrogen may be carried out in a solvent. Examples of the solvent include methanol, ethanol, propanol, ethyl acetate, toluene, diethyl ether, tetrahydrofuran and 1,4-dioxane. The used amount of the solvent is usually in a ratio of 0.1 to 50 parts by weight, based on 1 part by weight of the nitro compound represented by formula (1).

The reaction temperature is usually within the range of −20 to 150° C., and preferably within the range of 0 to 100° C. The reaction time is usually 0.1 to 72 hours, and preferably 1 to 24 hours.

The obtained reaction mixture is filtered, and the filtrate is concentrated, whereby the compound represented by formula (7) can be obtained. The obtained compound represented by formula (7) can be purified by usual purification means such as washing and distillation. The compound represented by formula (7) is converted to an acid addition salt such as hydrochloride using an acid such as hydrochloric acid, and then subjected to alkali treatment, thereby purifying the compound represented by formula (7).

Examples of the compound represented by formula (7) include 3-methyl-2-methoxymethyl-1-aminobenzene, 3-methyl-2-ethoxymethyl-1-aminobenzene, 2-isopropoxymethyl-3-methyl-1-aminobenzene, 2-propoxymethyl-3-methyl-1-aminobenzene, 2-(tert-butoxymethyl)-3-methyl-1-aminobenzene, 2-methoxymethyl-3-ethyl-1-aminobenzene, 2-ethoxymethyl-3-ethyl-1-aminobenzene, 2-isopropoxymethyl-3-ethyl-1-aminobenzene, 2-propoxymethyl-3-ethyl-1-aminobenzene, 2-(tert-butoxymethyl)-3-ethyl-1-aminobenzene, 2-methoxymethyl-3-cyclopropyl-1-aminobenzene, 2-ethoxymethyl-3-cyclopropyl-1-aminobenzene, 2-isopropoxymethyl-3-cyclopropyl-1-aminobenzene, 2-propoxymethyl-3-cyclopropyl-1-aminobenzene, 2-(tert-butoxymethyl)-3-cyclopropyl-1-aminobenzene, 2-methoxymethyl-1-aminobenzene, 2-ethoxymethyl-1-aminobenzene, 2-isopropoxymethyl-1-aminobenzene, 2-propoxymethyl-1-aminobenzene, 2-(tert-butoxymethyl)-1-aminobenzene, 2-methoxymethyl-3-chloro-1-aminobenzene, 2-ethoxymethyl-3-chloro-1-aminobenzene, 2-isopropoxymethyl-3-chloro-1-aminobenzene, 2-propoxymethyl-3-chloro-1-aminobenzene, 2-(tert-butoxymethyl)-3-chloro-1-aminobenzene, 2-methoxymethyl-3-bromo-1-aminobenzene, 2-ethoxymethyl-3-bromo-1-aminobenzene, 2-isopropoxymethyl-3-bromo-1-aminobenzene, 2-propoxymethyl-3-bromo-1-aminobenzene, 2-(tert-butoxymethyl)-3-bromo-1-aminobenzene, 2-methoxymethyl-3-fluoro-1-aminobenzene, 2-ethoxymethyl-3-fluoro-1-aminobenzene, 2-isopropoxymethyl-3-fluoro-1-aminobenzene, 2-propoxymethyl-3-fluoro-1-aminobenzene, 2-(tert-butoxymethyl)-3-fluoro-1-aminobenzene, 2-methoxymethyl-3-methoxy-1-aminobenzene, 2-ethoxymethyl-3-methoxy-1-aminobenzene, 2-isopropoxymethyl-3-methoxy-1-aminobenzene, 2-propoxymethyl-3-methoxy-1-aminobenzene and 2-(tert-butoxymethyl)-3-methoxy-1-aminobenzene.

EXAMPLES

Example 1

Under a nitrogen atmosphere, 605 mg of 2,3-dimethylnitrobenzene, 1.95 g of 1,2-dibromo-1,1,2,2-tetrachloroethane and 13.6 mL of a 20% sodium ethoxide-ethanol solution were mixed. The resulting mixture was stirred at room temperature for 17 hours. The resulting reaction mixture was acidified, and then extracted with ethyl acetate. The resulting organic layer was washed sequentially with water and saturated saline, dried over anhydrous sodium sulfate, and then concentrated under reduced pressure. The residue was subjected to a silica gel column chromatography to obtain 588 mg of 2-ethoxymethyl-3-methyl-1-nitrobenzene (yield of 75%).
$^1$H-NMR (CDCl$_3$) δ (ppm): 7.54 (1H, d, J=8.0 Hz), 7.39 (1H, d, J=7.1 Hz), 7.33-7.29 (1H, m), 4.65 (2H, s), 3.54 (2H, q, J=6.9 Hz), 2.48 (3H, s), 1.21 (3H, t, J=6.9 Hz)

Example 2

4.0 g of 2,3-dimethylnitrobenzene and 13.0 g of 1,2-dibromo-1,1,2,2-tetrachloroethane, and 12.0 g of methanol were mixed, and the mixture was heated at 65° C. At the same temperature, 17.6 g of a 5M sodium methoxide-methanol solution was added dropwise to the resulting mixture. Furthermore, 1.3 g of 1,2-dibromo-1,1,2,2-tetrachloroethane and 2.6 g of a 5 M sodium methoxide-methanol solution were added, and the mixture was stirred for 1 hour. After cooling the resulting reaction mixture to room temperature, a saturated aqueous ammonium chloride solution was added, and the mixture was concentrated under reduced pressure. The residue was diluted with ethyl acetate, and then separated to obtain an organic layer and an aqueous layer. The resulting aqueous layer was extracted with ethyl acetate to obtain an ethyl acetate layer. The ethyl acetate layer and the organic layer previously obtained were combined to obtain a solution containing 4.3 g of 2-methoxymethyl-3-methyl-1-nitrobenzene.
$^1$H-NMR (CDCl$_3$) δ (ppm): 7.57-7.54 (1H, m), 7.40 (1H, d, J=7.2 Hz), 7.34-7.29 (1H, m), 4.61 (2H, s), 3.38 (3H, s), 2.48 (3H, s)

Example 3

2.0 g of 2,3-dimethylnitrobenzene, 6.5 g of 1,2-dibromo-1,1,2,2-tetrachloroethane and 8.0 g of methanol were mixed and heated to 65° C. 2.6 g of potassium hydroxide was added to the resulting reaction mixture. Furthermore, 0.9 g of 1,2-dibromo-1,1,2,2-tetrachloroethane and 0.7 g of potassium hydroxide were added thereto and stirred for 2 hours. After cooling the resulting reaction mixture to room temperature, a saturated aqueous ammonium chloride solution was added, and the mixture was concentrated under reduced pressure. The residue was diluted with ethyl acetate and then separated to obtain an organic layer and an aqueous layer. The resulting aqueous layer was extracted with ethyl acetate to obtain an ethyl acetate layer. The ethyl acetate layer and the organic layer previously obtained were combined, and it was confirmed that a solution containing 2.17 g of 2-methoxymethyl-3-methyl-1-nitrobenzene was obtained.

Example 4

A mixture of 5 mg of 5% palladium-activated carbon and 0.5 g of methanol was added to 0.1 g of 2-methoxymethyl-3-methyl-1-nitrobenzene obtained in Example 2, and the mixture was stirred at room temperature for 1 hour, under a hydrogen atmosphere. The resulting reaction mixture was filtered, and it was confirmed that a solution containing 3-methyl-2-methoxymethyl-1-aminobenzene was obtained.
$^1$H-NMR (CDCl$_3$) δ (ppm): 2.33 (3H, s), 3.36 (3H, s), 4.12 (2H, s), 4.54 (2H, s), 6.55 (1H, d, J=8.0 Hz), 6.58 (1H, d, J=7.3 Hz), 7.00 (1H, t, J=7.7 Hz)

Example 5

Under a nitrogen atmosphere, 2.0 g of 2,3-dimethylnitrobenzene, 6.1 g of methanol and 10.2 g of a 28% sodium methoxide-methanol solution were mixed, and 5.3 g of bromotrichloromethane was added dropwise, and then the mixture was stirred at 50° C. for 15 hours. The resulting reaction mixture was acidified and then concentrated. Water and saline were added to the residue, and the mixture was extracted with ethyl acetate. The resulting organic layer was concentrated under reduced pressure to obtain 2.0 g of a brown oily matter containing 2-methoxymethyl-3-methyl-1-nitrobenzene. The oily product was analyzed by high performance liquid chromatography, and the yield of 2-methoxymethyl-3-methyl-1-nitrobenzene calculated on the basis of the resulting area percentage value was 69%.

Example 6

Under a nitrogen atmosphere, 2.0 g of 2,3-dimethylnitrobenzene, 10.1 g of methanol and 5.12 g of a 28% sodium methoxide-methanol solution were mixed, and 8.9 g of tetrabromomethane was added, and then the mixture was stirred at 70° C. for 17 hours to obtain a reaction mixture containing 2-methoxymethyl-3-methyl-1-nitrobenzene. The reaction mixture was analyzed by high performance liquid chromatography, and the area percentage value of 2-methoxymethyl-3-methyl-1-nitrobenzene was 17%.

Example 7

Under a nitrogen atmosphere, 116.3 g of a 28% sodium methoxide-methanol solution was added dropwise to a mixture of 25.0 g of 2,3-dimethylnitrobenzene and 57.5 g of bromotrichloromethane at 70° C. over 8 hours. The resulting mixture was stirred at the same temperature for further 3 hours. After concentrating the resulting reaction mixture, water was added to the residue, and the mixture was extracted with toluene. The resulting organic layer was concentrated under reduced pressure to obtain 29.0 g of an orange oily product containing 2-methoxymethyl-3-methyl-1-nitrobenzene. Yield: 91%.

Example 8

Under a nitrogen atmosphere, 43.0 g of bromotrichloromethane and 167.9 g of a 20% sodium hydroxide-methanol solution were added dropwise to 25.0 g of 2,3-dimethylnitrobenzene at the same time at 70° C. over 8 hours, and the mixture was stirred at the same temperature for further 3 hours. The resulting reaction mixture was concentrated, water was added to the residue, and the mixture was extracted with toluene. The resulting organic layer was concentrated to obtain 68.4 g of an orange oily product containing 2-methoxymethyl-3-methyl-1-nitrobenzene. Yield: 86%.

Example 9

Under a nitrogen atmosphere, 165.0 g of 2-methoxymethyl-3-methyl-1-nitrobenzene, 331.0 g of methanol and 4.2 g of 5% palladium-carbon (55% hydrous) were added to a flask. After replacing nitrogen in the flask with hydrogen, the mixture in the flask was stirred at 50° C. for 15 hours. The resulting reaction mixture was filtered, and the resulting filtrate was concentrated under reduced pressure. Toluene was added to the residue, and further concentrated to obtain 152.8 g of an orange oily product containing 2-methoxymethyl-3-methylaniline. The yield of 2-methoxymethyl-3-methylaniline was 99%.

INDUSTRIAL APPLICABILITY

According to the present invention, it is possible to produce a nitro compound represented by formula (1). The nitro compound represented by formula (1) can be a raw material for producing a compound represented by formula (7) that is useful as a production intermediate of a tetrazolinone compound having an activity for controlling pests.

The invention claimed is:
1. A method for producing a nitro compound of formula (1):

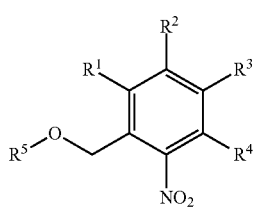

(1)

wherein $R^1$, $R^2$, $R^3$ and $R^4$ each independently represent a hydrogen atom, an alkyl group having 1 to 6 carbon atoms optionally having a halogen atom or atoms, a cycloalkyl group having 3 to 6 carbon atoms, a halogen atom, an alkoxy group having 1 to 6 carbon atoms, an alkylthio group having 1 to 6 carbon atoms, an alkylamino group having 1 to 6 carbon atoms or an aryl group having 6 to 12 carbon atoms, and $R^5$ represents an alkyl group having 1 to 12 carbon atoms, a cycloalkyl group having 3 to 6 carbon atoms or an alkenyl group having 2 to 6 carbon atoms, comprising a step of reacting a compound of formula (2):

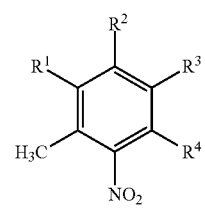

(2)

wherein $R^1$, $R^2$, $R^3$ and $R^4$ have the same meanings as above,
at least one selected from the group consisting of a compound of formula (3):

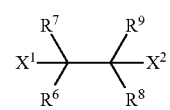

(3)

wherein $X^1$ and $X^2$ each independently represent a chlorine atom, a bromine atom or an iodine atom, $R^6$, $R^7$, $R^8$ and $R^9$ each independently represent a halogen atom, an alkyl group having 1 to 6 carbon atoms optionally having a halogen atom or atoms, an alkenyl group having 2 to 6 carbon atoms, an alkoxy group having 1 to 6 carbon atoms, an alkoxycarbonyl group having 2 to 6 carbon atoms, a hydrogen atom or a cyano group, provided that $X^1$, $X^2$, $R^6$, $R^7$, $R^8$ and $R^9$ are not all the same, and $R^7$ and $R^9$ may be bonded each other to form a ring together with the carbon atoms to which they are bonded,
and a compound of formula (3'):

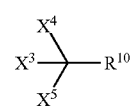

(3')

wherein $X^3$, $X^4$ and $X^5$ represent a halogen atom, and $R^{10}$ represents a hydrogen atom, a nitro group, a halogen atom, an alkyl group having 1 to 6 carbon atoms optionally having a halogen atom or atoms, an alkoxy group having 1 to 6 carbon atoms or an aryl group having 6 to 12 carbon atoms,
and a compound of formula (4):

$$R^5\text{—OM} \qquad (4)$$

wherein $R^5$ has the same meaning as above, and M represents an alkali metal atom.

2. The method for producing a nitro compound according to claim 1 comprising a step of reacting the compound of formula (2), the compound of formula (3), and the compound of formula (4).

3. A method for producing a nitro compound represented by formula (1):

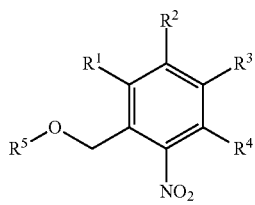
(1)

wherein $R^1$, $R^2$, $R^3$ and $R^4$ each independently represent a hydrogen atom, an alkyl group having 1 to 6 carbon atoms optionally having a halogen atom or atoms, a cycloalkyl group having 3 to 6 carbon atoms, a halogen atom, an alkoxy group having 1 to 6 carbon atoms, an alkylthio group having 1 to 6 carbon atoms, an alkylamino group having 1 to 6 carbon atoms or an aryl group having 6 to 12 carbon atoms, and $R^5$ represents an alkyl group having 1 to 12 carbon atoms, a cycloalkyl group having 3 to 6 carbon atoms or an alkenyl group having 2 to 6 carbon atoms, comprising a step of reacting a compound of formula (5):

wherein $R^5$ has the same meaning as above,
a compound of formula (6):

wherein M represents an alkali metal atom,
a compound of formula (2):

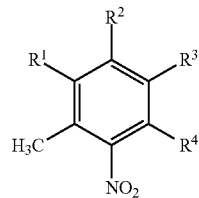
(2)

wherein $R^1$, $R^2$, $R^3$ and $R^4$ have the same meaning as above,
and at least one selected from the group consisting of a compound of formula (3):

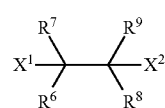
(3)

wherein $X^1$ and $X^2$ each independently represent a chlorine atom, a bromine atom or an iodine atom, $R^6$, $R^7$, $R^8$ and $R^9$ each independently represent a halogen atom, an alkyl group having 1 to 6 carbon atoms optionally having a halogen atom or atoms, an alkenyl group having 2 to 6 carbon atoms, an alkoxy group having 1 to 6 carbon atoms, an alkoxycarbonyl group having 2 to 6 carbon atoms, a hydrogen atom or a cyano group, provided that $X^1$, $X^2$, $R^6$, $R^7$, $R^8$ and $R^9$ are not all the same, and $R^7$ and $R^9$ may be bonded each other to form a ring together with the carbon atoms to which they are bonded, and a compound of formula (3'):

(3')

wherein $X^3$, $X^4$ and $X^5$ represent a halogen atom, and $R^{10}$ represents a hydrogen atom, a nitro group, a halogen atom, an alkyl group having 1 to 6 carbon atoms optionally having a halogen atom or atoms, an alkoxy group having 1 to 6 carbon atoms or an aryl group having 6 to 12 carbon atoms.

4. The method for producing a nitro compound according to claim 3 comprising a step of reacting the compound of formula (5), the compound of formula (6), the compound of formula (2), and the compound of formula (3).

5. The production method according to claim 4, wherein $X^1$ and $X^2$ are the same.

6. The production method according to claim 4, wherein the compound of formula (3) is 1,2-dibromo-1,1,2,2-tetrachloroethane or 1,2-dibromo-1,1,2,2-tetrafluoroethane.

7. The method for producing a nitro compound according to claim 1 comprising a step of reacting the compound of formula (2), the compound of formula (3'), and the compound of formula (4).

8. The method for producing a nitro compound according to claim 3 comprising a step of reacting the compound of formula (5), the compound of formula (6), the compound of formula (2), and the compound of formula (3').

9. The method for producing a nitro compound according to claim 7, wherein $R^{10}$ is a halogen atom.

10. The method for producing a nitro compound according to claim 7 wherein the compound of formula (3') is tetrabromomethane or bromotrichloromethane.

11. A method for producing a compound of formula (7):

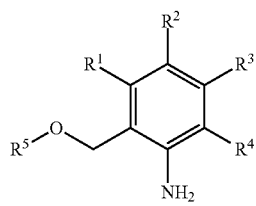
(7)

wherein $R^1$, $R^2$, $R^3$, $R^4$ and $R^5$ have the same meanings as above,
comprising obtaining a nitro compound of formula (1) by the production method as defined in claim 1, and reducing the nitro compound of formula (1).

12. A nitro compound of formula (8):

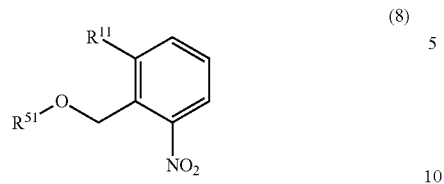

(8)

wherein $R^{11}$ represents an alkyl group having 1 to 3 carbon atoms or a cycloalkyl group having 3 to 4 carbon atoms, and $R^{51}$ represents an alkyl group having 1 to 12 carbon atoms, a cycloalkyl group having 3 to 6 carbon atoms or an alkenyl group having 2 to 6 carbon atoms.

13. The nitro compound according to claim 12, wherein $R^{11}$ is a methyl group, and $R^{51}$ is an alkyl group having 1 to 6 carbon atoms.

14. The nitro compound according to claim 12, wherein $R^{11}$ is a methyl group, and $R^{51}$ is a methyl group or an ethyl group.

* * * * *